United States Patent [19]

Thizy et al.

[11] 4,163,782
[45] Aug. 7, 1979

[54] FUNGICIDAL COMPOSITIONS CONTAINING DISUBSTITUTED PHOSPHONATES

[75] Inventors: André Thizy, Ecully; Jean-Claude Debourge, Lyon, both of France

[73] Assignee: Philagro, France

[21] Appl. No.: 941,377

[22] Filed: Sep. 12, 1978

Related U.S. Application Data

[63] Continuation of Ser. No. 799,784, May 23, 1977, abandoned, which is a continuation of Ser. No. 555,293, Mar. 4, 1975, abandoned.

[30] Foreign Application Priority Data

Mar. 8, 1974 [FR] France .................. 74 08995

[51] Int. Cl.² .................. A01N 9/00; A01N 9/36
[52] U.S. Cl. .................. 424/217; 424/203; 424/222; 424/223; 424/DIG. 8
[58] Field of Search .............. 424/203, 217, 222, 223, 424/DIG. 8

[56] References Cited

U.S. PATENT DOCUMENTS 2,866,732  12/1958  Hoff et al. .................. 424/223 X

FOREIGN PATENT DOCUMENTS 1216278  5/1966  Fed. Rep. of Germany .
459199  2/1970  Japan .
4711519  11/1972  Japan .
699154  10/1953  United Kingdom .
1051965  12/1966  United Kingdom .

OTHER PUBLICATIONS

McCombie et al., J. of the Chem. Society, London, (1945), pp. 380–382.

Primary Examiner—Allen J. Robinson
Attorney, Agent, or Firm—Robert E. Burns; Emmanuel J. Lobato; Bruce L. Adams

[57] ABSTRACT

Compositions are described which are suitable for use in controlling parasitic fungi, especially mildews, in plants and which contain as their active material at least one compound corresponding to the general formula:

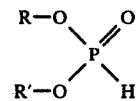

in which
R and R', which may be the same or different, represent a linear or branched alkyl radical of 1–18 carbon atoms, which may optionally be substituted, preferably by halogens or hydroxy groups, an optionally substituted cyclohexyl or phenyl radical; a heterocyclic radical connected to an oxygen atom adjacent the phosphorus by an aliphatic chain of 1 or 2 carbon atoms.

10 Claims, No Drawings

FUNGICIDAL COMPOSITIONS CONTAINING DISUBSTITUTED PHOSPHONATES

This is a continuation, of application Ser. No. 799,784, filed May 23, 1977, now abandoned, which in turn was a continuation of Ser. No. 555,293, filed on Mar. 4, 1975 and now abandoned.

FIELD OF THE INVENTION

This invention relates to fungicidal compositions. More particularly it relates to fungicidal compositions based on diesters of phosphonic acid (or phosphonates) and their salts also referred to as dialkyl or aryl phosphites.

THE INVENTION

The invention relates to compositions which are suitable for use in controlling parasitic fungi, especially mildews, in plants and which contain as their active material at least one compound corresponding to the general formula:

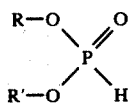

in which
R and R', which may be the same or different, represent a linear or branched alkyl radical of 1–18 carbon atoms, which may optionally be substituted, preferably by halogens or hydroxy groups; an optionally substituted cyclohexyl or phenyl radical; or a heterocyclic radical connected to an oxygen atom adjacent the phosphorus by an aliphatic chain of 1 or 2 carbon atoms.

One preferred sub-group comprises compounds of the following formula:

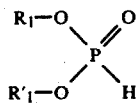

in which
$R_1$ and $R'_1$, which may be the same or, preferably, different, represent a linear or branched, optionally halogen- or hydroxyl-substituted alkyl radical containing 1 to 4 carbon atoms, the alkyl chain optionally being interrupted by an oxygen atom.

DETAILED DESCRIPTION

Some of these compounds are known. In particular, GB-PS No. 1,051,965 describes a process for the preparation of phosphonic acid esters in which one of the substituents is a lower alkyl radical and the other an optionally substituted alkyl, aralkyl or aryl radical. These compounds, like their corresponding phosphates, have pesticidal properties, but none of these pesticidal properties is illustrated in the above-mentioned GB-PS.

It has now been found that the compounds in compositions according to this invention show excellent fungicidal properties and, in particular, are remarkably active against mildews, such as mildew of the vine (grape), tobacco mildew and hop mildew.

The compounds for the composition of this invention may be obtained by the methods described in Hoben-Weyl XII/2, pp. 20–37. The syntheses may differ according to whether it is desired to obtain symmetrical or asymmetrical phosphonic esters.

Some symmetrical compounds are produced on an industrial scale and are commercially available and include in particular O,O-dimethyl phosphonate, O,O-diethyl phosphonate, O,O-di-n-butyl phosphonate, O,O-di-n-hexyl phosphonate, O,O-di-2-ethyl-n-hexyl phosphonate, O,O-di-n-octyl phosphonate, O,O-di-n-dodecyl phosphonate, O,O-n-hexadecyl phosphonate, O,O-diphenyl phosphonate.

The other active compounds may be prepared by the method described by Mc COMBIE in Journal of the Chemical Society, LONDON (1945), page 380, in accordance with the following scheme:

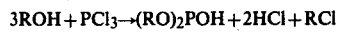

O,O-Diethyl phosphonate is prepared in this way: 1 mol. of phosphorus trichloride in solution in 150 ml. of carbon tetrachloride is added with stirring to a solution of 3 mols. of ethanol in 225 ml. of carbon tetrachloride. The mixture is heated for 30 minutes to 90° C. Dry nitrogen is then bubbled through the reaction mixture in order to remove the volatile compounds. Following removal of the solvent, the product is distilled in vacuo.

Yield: 93% b.p.$_{14\ mm\ Hg}$: 73°–74° C. $n_D^{20}$: 1.4080

By this method the compounds identified along with their characteristics in the following Table were synthesized.

| Compounds | Physical characteristics | Yield |
|---|---|---|
| O,O-di-n-propyl phosphonate | b.p.$_{19\ mm\ Hg}$: 99°–100° C. $n_D^{20}$: 1.4175 | 89% |
| O,O-di-isopropyl phosphonate | b.p.$_{8\ mm\ Hg}$: 64°–67° C. $n_D^{20}$: 1.4095 | 70% |
| O,O-di-2-chlorethyl phosphonate | b.p.$_{1\ mm\ Hg}$: 99° C. $n_D^{20}$: 1.4175 | 88% |
| O,O-di-methoxy ethyl phosphonate | b.p.$_{0.13\ mm\ Hg}$: 150° C. $n_D^{20}$: 1.4310 | 70% |
| O,O-di-cyclohexyl phosphonate | b.p.$_{0.06\ mm\ Hg}$: 115°–120° C. $n_D^{20}$: 1.4762 | 20% |
| O,O-di-tetrahydro-furfuryl phosphonate | $n_D^{20}$: 1.474 | 50% |

In cases where R and R' are long-chain substituents, it is preferred to react phosphorous acid with an alcohol under reflux in toluene, cf. GB-PS No. 699,154:

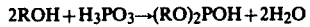

The asymmetrical compounds are prepared by the method described in GB-PS No. 1,051,965, referred to above; or by the method described in DT-PS No. 1,216,278 which comprises reacting a salt of a monoester of phosphonic acid with a haloformate in accordance with the following scheme:

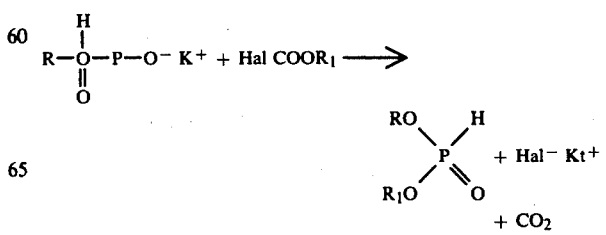

O-Methyl, O-ethyl phosphonate was prepared by this method:

Methyl chloroformate is reacted with sodium ethyl phosphite in methylene chloride at ambient temperature. After filtration and evaporation of the solvent, the product is distilled in vacuo.

b.p.$_{12\ mm.\ Hg}$: 63°–64° C. n$_D^{20}$ 1.4050 yield: 72%

The Examples illustrate the fungicidal properties of the following compounds:

(1) O,O-dimethyl phosphonate
(2) O,O-diethyl phosphonate
(3) O,O-di-n-propyl phosphonate
(4) O,O-diisopropyl phosphonate
(5) O,O-di-n-butyl phosphonate
(6) O,O-dimethoxy ethyl phosphonate
(7) O,O-diphenyl phosphonate
(8) O,O-dicyclohexyl phosphonate
(9) O-methyl, O-ethyl phosphonate

EXAMPLE 1

In vivo test on *Plasmopara viticola* in vine plants (a) Preventive treatment

The leaves of pot-grown vine plants (Gamay variety) are sprayed underneath using a spray gun with 40 cc of an aqueous suspension of a wettable powder having the following composition (by weight):

active material to be tested . . . 20%
deflocculant (calcium lignosulphate) . . . 5%
wetting agent (sodium alkyl aryl sulphonate) . . . 1%
filler (aluminium silicate) . . . 74% in the required dilution containing the active material to be tested in the required dose. Each test was repeated three times.

After 48 hours, the plants are contaminated by spraying the leaves underneath with an aqueous suspension of approximately 80,000 units/cc. of spores of the fungus.

The pots are then placed in an incubation cell at 20° C./100% relative humidity for a period of 48 hours.

The plants are inspected 9 days after infestation.

Under these conditions, it was found that, in a dose of 0.5 g/l, compounds 1, 2, 6, 8 and 9 afford total protection, whilst compounds 3 and 5 afford good protection.

In addition, it was found that none of the compounds tested showed the least phytotoxicity.

(b) Treatment after Contamination

The procedure is as described in (a) above, except that the plants are initially contaminated and then treated with the active material to be tested, the plants are inspected and results evaluated 9 days after contamination.

Under these conditions, it was found that, in doses of 1 g/l, compounds 1, 2, 3 6 and 8 completely stop the growth of the mildew on the vine plants.

EXAMPLE 2

Systemic test by root absorption on vine mildew

Several vine stocks (Gamay variety) each accommodated in a pot containing vermiculite and a nutritive solution are sprinkled with 40 cc. of a solution containing 0.5 g/l of the material to be tested. After 2 days, the vine is contaminated with an aqueous suspension containing 100,000 spores/cc. of *Plasmopara viticola*. The spore-infected plants are left to incubate for 48 hours at 20° C./100% relative humidity. The degree of infestation is assessed after about 9 days in relation to an infested control which has only been sprinkled with 40 cc. of distilled water.

Under these conditions, it was found that compounds 1, 2, 3, 4, 5 and 9, absorbed by the roots, afford total protection to the vine leaves against mildew, which demonstrates clearly the systemic nature of these compounds. The controls showed complete infection.

EXAMPLE 3

Systemic test by leaf absorption on mildew of the vine

Vine stocks (Gamay variety) each accommodated in a pot containing a mixture of clean soil and sand, are treated at the 7-leaf stage.

The treatment is carried out by spraying the lowest 4 leaves underneath with 40 cc of an aqueous suspension of a wettable powder containing 2.5 g/l of the active material to be tested.

After 2 days, the entire vine is contaminated by spraying with an aqueous suspension containing approximately 100,000 spores/cc. of *Plasmopara viticola*. The spores are then left to incubate for 48 hours in a room at 20° C./100% relative humidity. The degree of infestation is assessed, after about 9 days, from the 5th to 7th leaves from the bottom in relation to a control which has been treated with distilled water. Under these conditions, it was found that compounds, 1, 6, 7, 8 and 9 sprayed on the lower leaves afford total protection to the upper leaves of the vine against mildew.

All these Examples clearly demonstrate the remarkable anti-mildew activity of the compounds according to the invention, by a topical and systemic activity which both prevent and stop growth of the fungus. Accordingly, these compounds may be used both for the prophylactic or preventive treatment and for the curative treatment of plants susceptible to fungus disease caused, by phycomycetes and ascomycetes, and in particular, for the protection of vegetation such as, in particular, vines, hops or tobacco against mildews of the *Plasmopara viticola*, *Peronospora tabacci* or *Pseudo peroponospora humili* type.

In addition, these compounds may be used with advantage in compositions in admixture with other known fungicides, such as metal dithiocarbamates (manebe, zinebe, mancozebe), basic salts or hydroxides of copper (oxy chloride, oxy sulphate), (tetrahydro) phthalimides (captane, captafol, folpel), methyl N-(1-butyl carbamoyl)-2-benzimidazole carbamate (benomyl), 1,2-di-(3-methoxy or ethoxy)-2-carbonyl thioureidobenzenes (thiophanates), methyl 2-benzimidazole carbamate, etc., either in order to complete the spectrum and/or range of activity of the compounds according to the invention or to increase their persistence.

It has also been found that these compounds may be mixed into compositions with other fungicidal phosphorus derivatives having anti-mildew activity, especially the optionally substituted 2-hydroxy-1,3,2-dioxaphospholanes described in French Patent Application No. 73-01.803 and its Addition 73.37994; and with phosphorous acid and its salts, as described in French Patent Application No. 73-45.627.

The doses in which the compounds according to the invention are used may vary within wide limits, depending upon the degree of infection, upon the virulence of the fungus and upon the climatic conditions.

Compositions containing from 0.01 to 5 g/l of active material in liquid vehicles are generally suitable.

For their practical application, the compounds according to the invention are rarely used on their own. Instead, they generally form part of formulations which, as a rule, contain a diluent vehicle or support and/or a surfactant in addition to the active material according to the invention.

In the context of the invention, a support inorganic, organic or mineral; liquid, solid or aerosol; natural or synthetic material with which the active material is associated to facilitate its application to the plant, to seeds or to soil, or its application transportation or handling. The support can be solid (clays, natural or synthetic silicates, resins, waxes, solid fertilizers) or fluid (water, alcohols, ketones, petroleum fractions, chlorinated hydrocarbons, emulsions, liquified gases). Aerosol droplets or particles may also be supports.

The surfactants can be an ionic or non-ionic emulsifier, dispersant or wetting agent such as, for example, salts of polyacrylic acids and lignin sulphonic acids, condensates of ethylene oxide with fatty alcohols, fatty acids or fatty amines.

The compositions according to the invention may be prepared in the form of wettable powders, soluble powders, dusting powders, granulates, solutions, emulsifiable concentrates, emulsions, suspended concentrates and aerosols.

The wettable powders according to the invention can be prepared in such a way that they contain from 20 to 95% by weight of the active material, and they normally contain, in addition to a solid support, from 0 to 5% by weight of a wetting agent, from 3 to 10% by weight of one or more stabilizers and/or other additives, such as penetration agents, adhesives or antilumping agents, diluents, colorants, etc.

One example of the composition of a wettable powder is given below:

active material . . . 50%
calcium lignosulphate (deflocculant) . . . 5%
anionic wetting agent (alkylaryl sulphonate) . . . 1%
antilumping silica . . . 5%
kaolin (filler) . . . 39%

The water-soluble powders are obtained in the usual way by mixing from 20 to 95% by weight of the active material with 0 to 10% of an antilumping filler, the balance being made up by a solid water-soluble support, especially a salt.

One example of the composition of a soluble powder is given below:

active material . . . 70%
anionic wetting agent . . . 0.5%
antilumping silica . . . 5%
sodium sulphate (soluble support) . . . 24.5%

Aqueous dispersions, concentrates and emulsions, for example compositions obtained by diluting with water a wettable powder or an emulsifiable concentrate according to the invention, are included within the general scope of the invention. These emulsions can be of the water-in-oil type or of the oil-in-water type, and can range from a thick consistency resembling that of a "mayonnaise" to water-like consistency, the acting material may also be incorporated into gels or pastes for local topical application.

The compositions according to the invention may contain other ingredients, for example protective colloids, adhesives or thickeners, thixotropic agents, stabilizers or sequestrants, as well as other active materials known to have pesticidal properties especially acaricides or insecticides. The latter formulations are useful for controlling both the fungal disease and its insect vectors.

The above detailed description and Examples are merely illustrative of presently preferred modes of the invention. All equivalents mentioned or art-recognized are intended for inclusion in the practice of this invention.

We claim:

1. A method of controlling plant fungus which comprises applying to said fungus a fungicidally effective amount of a composition containing as an active fungicidal ingredient at least one compound of the formula

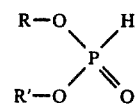

in which R and R' may be the same or different and each represents a linear or branched alkyl radical of 1 to 4 carbon atoms, optionally interrupted by an oxygen atom; phenyl; tetrahydrofurfuryl or cyclohexyl radical, in combination with an agriculturally acceptable vehicle.

2. The method as claimed in claim 1 wherein the radicals R and R' of said compound are the same.

3. The method as claimed in claim 1 wherein O,O-dimethyl phosphonate is the active ingredient.

4. The method as claimed in claim 1 O,O-diethyl phosphonate is the active ingredient.

5. The method as claimed in claim 1 O,O-dimethoxyethyl phosphonate is the active ingredient.

6. The method as claimed in claim 1, wherein the fungus disease is a mildew.

7. The method as claimed in claim 1, wherein said composition contains, in addition to fungicidally effective amounts of said active ingredient, other fungicidally-active ingredients in fungicidally effective amounts.

8. The method according to claim 1, wherein said active fungicidal ingredient is O,O-di-n-propyl phosphonate.

9. The method according to claim 1, in which said composition applied to said fungus is an aqueous dilution of a wettable powder containing about 20 to 95% by weight of said active fungicidal ingredient, 0 to 5% by weight of a wetting agent, 3 to 10% by weight of at least one reagent, selected from the group consisting of a stabilizer, penetration agent, adhesive, antilumping agent, diluent, and colorant, any remaining part being inert solid carrier.

10. The method according to claim 1, in which said fungal disease is a mildew and said composition applied to said fungus contains about 0.5 to 5 g. per liter of said active ingredient.

* * * * *